US010520515B2

(12) United States Patent
Manneh et al.

(10) Patent No.: US 10,520,515 B2
(45) Date of Patent: Dec. 31, 2019

(54) GLYCATED PROTEIN ASSAY

(71) Applicant: BIO-RAD LABORATORIES, INC., Hercules, CA (US)

(72) Inventors: Victor Manneh, Hercules, CA (US); Sergei Svarovsky, Hercules, CA (US); Anthony Prestigiacomo, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 378 days.

(21) Appl. No.: 15/127,706

(22) PCT Filed: Mar. 20, 2015

(86) PCT No.: PCT/US2015/021865
§ 371 (c)(1),
(2) Date: Sep. 20, 2016

(87) PCT Pub. No.: WO2015/143394
PCT Pub. Date: Sep. 24, 2015

(65) Prior Publication Data
US 2017/0176463 A1    Jun. 22, 2017

Related U.S. Application Data

(60) Provisional application No. 61/968,297, filed on Mar. 20, 2014.

(51) Int. Cl.
*G01N 33/558* (2006.01)
*G01N 33/72* (2006.01)
(Continued)

(52) U.S. Cl.
CPC ......... *G01N 33/723* (2013.01); *G01N 33/558* (2013.01); *G01N 33/582* (2013.01);
(Continued)

(58) Field of Classification Search
None
See application file for complete search history.

(56) References Cited

U.S. PATENT DOCUMENTS

| 5,110,745 A | 5/1992 | Kricka et al. |
|---|---|---|
| 7,807,401 B2 | 10/2010 | Kobold et al. |

(Continued)

FOREIGN PATENT DOCUMENTS

| CN | 101490558 A | 7/2009 |
|---|---|---|
| CN | 101622541 A | 1/2010 |

(Continued)

OTHER PUBLICATIONS

Extended European Search Report dated Jul. 18, 2017 in EP Patent Application No. 15765809.7. 8 pages.
(Continued)

*Primary Examiner* — Rebecca L Martinez
(74) *Attorney, Agent, or Firm* — Kilpatrick Townsend & Stockton LLP

(57) ABSTRACT

Methods, devices, and reagents are described for performing assays for hemoglobin A1e, glycated albumin, and other glycated proteins. The methods involve a ratio determination between glycated protein and non-glycated protein. In some applications, the assay utilizes LOCI for signal generation. This invention is directed to assays and corresponding devices and reagents for detection of glycated protein, particularly including glycated hemoglobin. As is generally understood, such detection is useful in the management of blood glucose levels in diabetic patients and for monitoring the status of pre-diabetic individuals.

18 Claims, 4 Drawing Sheets

(51) Int. Cl.
*G01N 33/68* (2006.01)
*G01N 33/58* (2006.01)

(52) U.S. Cl.
CPC ..... *G01N 33/6842* (2013.01); *G01N 2333/47* (2013.01); *G01N 2333/765* (2013.01)

(56) References Cited

U.S. PATENT DOCUMENTS

| | | | |
|---|---|---|---|
| 2003/0003602 | A1 | 1/2003 | Vogt et al. |
| 2008/0145272 | A1 | 6/2008 | Feaster et al. |
| 2009/0099269 | A1 | 4/2009 | Rigby et al. |
| 2011/0070658 | A1 | 3/2011 | Rutter et al. |
| 2011/0117670 | A1* | 5/2011 | Walker ............. C07K 16/18 436/501 |
| 2011/0118183 | A1 | 5/2011 | Bolt et al. |
| 2013/0203174 | A1 | 8/2013 | DiMagno |
| 2014/0073532 | A1 | 3/2014 | Walker et al. |

FOREIGN PATENT DOCUMENTS

| | | |
|---|---|---|
| CN | 102640002 A | 8/2012 |
| CN | 102998463 A | 3/2013 |
| CN | 103163297 A | 6/2013 |
| EP | 0455225 A2 | 11/1991 |
| EP | 1914315 | 2/2013 |
| EP | 2657681 | 10/2013 |
| RU | 2377069 C2 | 12/2009 |
| WO | 9208984 | 5/1992 |
| WO | 9962918 A1 | 12/1999 |
| WO | 2009099269 A1 | 8/2009 |
| WO | 2009156511 A2 | 12/2009 |
| WO | 2010009459 A1 | 1/2010 |

OTHER PUBLICATIONS

Khan et al., "Diabetic Retinopathy Gluco-Oxidation of Proteins in Etiology of Diabetic Retinopathy", Diabetic Retinopathy, Chap!. 2, Retrieved from the Internet<www.intechopen.com/books/diabetic-retinopathy/gluco-oxidation-of-proteins-in-etiology-of-diabetic-retinopathy> on May 20, 2015 (May 20, 2015). entire document, Feb. 24, 2012, pp. 31-52.

Ullman et al., "Chapter 2.3 Homogeneous Immunoassays", The Immunoassay Handbook: Theory and applications of ligand binding, ELISA and related techniques, 4th Ed., Feb. 14, 2013, pp. 67-87.

Zin et al., "Haemoglobin A1c: comparing performance of two point of care devices with laboratory analyser," BMC Research Notes, Dec. 18, 2013, vol. 06, pp. 1-4. entire document.

PCT/US2015/021865 , "International Search Report and Written Opinion", dated Jun. 23, 2015, 18 pages.

English translation of Office Action dated Nov. 16, 2017 in CN Patent Application No. 201580026471.2. 10 pages.

Ullman, Edwin F. et al.; "Luminescent oxygen channeling assay (LOCI): sensitive, broadly applicable homogeneous immunoassay method"; Clinical Chemistry; 1996; vol. 42, No. 9; pp. 1518-1526.

Extended European Search Report dated Jul. 31, 2018 in EP Patent Application No. 18181951.7. 9 pages.

Eglen, Richard M. et al.; "The Use of AlphaScreen Technology in HTS: Current Status"; Current Chemical Genomics; 2008; vol. 1; pp. 2-10 (10 pages).

Wen, Chu-Ling et al.; "Development of an AlphaLISA assay to quantify serum core-fucosylated E-cadherin as a metastatic lung adenocarcinoma biomarker"; Journal of Proteomics; 2012; vol. 75, No. 13; pp. 3963-3976.

Monneret, D. et al.; "Evaluation of LOCI technology-based thyroid blood tests on the Dimension Vista analyzer"; Clinical Biochemistry; 2013; vol. 46; pp. 1290-1297.

English translation of Office Action dated Nov. 2, 2018 in RU Patent Application No. 2016141232. 8 pages.

\* cited by examiner

GLYCATED PROTEIN ASSAY

CROSS-REFERENCE TO RELATED PATENT APPLICATIONS

The present application claims benefit of priority to U.S. Provisional Patent Application No. 61/968,297 filed Mar. 20, 2014, which is incorporated by reference.

FIELD OF THE INVENTION

The present invention relates to an assay for glycated proteins.

BACKGROUND OF THE INVENTION

The following discussion is provided solely to assist the understanding of the reader, and does not constitute an admission that any of the information discussed or references cited constitute prior art to the present invention.

Control of blood glucose concentrations in diabetic patients has been shown to decrease the frequency and severity of long-term microvascular and neurologic complications of the disease. It has been found that the rate of formation of glycated hemoglobin is directly related to the glucose concentration in blood. As a result, in the management of glucose levels, measurement of glycated hemoglobin is used to determine how well blood glucose concentration has been managed over extended time periods.

Typically, the average lifetime for red blood cells is about 90-120 days. Therefore, determination of the percent glycation of hemoglobin correlates with the average glucose concentration during that period of time, and especially over the previous 2-3 months. Therefore, the percent glycated hemoglobin is an indicator of glycemic control over that time period.

Hemoglobin variants, such as HbS, HbC, HbD, HbE, may have a shorter average lifetime and different glycation rates and can have an effect on the correlation of % HbA1C to average glucose concentration, hence effecting the clinical value of the HbA1C result.

Knowing if a common variant is present is an important factor when assessing glycemic control, especially in a screening environment.

It has also been found that glucose attaches to non-hemoglobin proteins in blood, for example the abundant protein, albumin. Since the circulating half-life for albumin is about 20 days, the concentration (or ratio) of glycated albumin is a measure of the average glucose concentration over the previous 2-3 weeks.

Some methods to determine the concentration or percent of glycated proteins have utilized dihydroxyboryl compounds which bind to the 1,2 cis diols of the carbohydrate of glycated proteins to separate them from non-glycated proteins. Such methods include those described in U.S. Pat. Nos. 4,269,605, 5,284,777, 5,110,745, 4,861,728 PCT Appl. WO 96/03657), and PCT application WO 9840750, which are incorporated herein by reference in their entireties.

BRIEF SUMMARY OF THE INVENTION

This invention is directed to assays and corresponding devices and reagents for detection of glycated protein, particularly including glycated hemoglobin. As is generally understood, such detection is useful in the management of blood glucose levels in diabetic patients and for monitoring the status of pre-diabetic individuals. Assays are described herein which provide rapid, high precision assays amenable to use in variety of settings, including in point-of-care settings.

This invention describes an assay format for the accurate and precise quantitation of percent Hemoglobin A1C (i.e., glycated hemoglobin). In addition, in some embodiments this multiplexed assay will detect if there is a common variant present in the sample being tested. In some embodiments, the assay provides a quantitative result for the percent hemoglobin A1C by measuring both hemoglobin A1C and total hemoglobin separately and then taking the ratio of the two results. Common Hemoglobin variants HbS, HbC, HbD, and HbE can be measured quantitatively, semi-quantitatively, or qualitatively. As desired, hemoglobin variant results can be combined or expressed separately such that the presence or quantity of each variant is provided. Such a detection is useful in the screening for diabetic patients and for monitoring the status of diabetic individuals. Assays are described herein which provide rapid, high precision assays amenable to use in variety of settings, including in point-of-care settings.

A first aspect of the invention concerns a method for determining the fraction of a glycated protein in a sample. The method involves contacting (i) a labeled, specific binding member specific for total protein or a peptide corresponding to total protein (i.e., the total amount of a specific protein whether in glycated or unglycated form, e.g., glycated or unglycated hemoglobin) or for un-glycated protein or peptide, and (ii) a labeled, specific binding member specific for glycated protein (e.g., hemoglobin A1c) or peptide with:

a. a sample containing said protein or a peptide of the protein susceptible to glycation; and b. said protein or peptide or an unglycated version of the protein or peptide, any of which are competitor proteins and are not from the sample, and in some embodiments are biotinylated; and/or c. a glycated version of the protein or peptide, either of which is a competitor protein and is not from the sample, and in some embodiments are biotinylated.

The method then involves detecting a plurality of signals, with at least a first signal indicative of the level of glycated protein (e.g., A1c), and at least a second signal indicative of the level of unglycated protein or total protein (e.g., total amount of hemoglobin (glycated and unglycated) and optionally hemoglobin variants); and determining a ratio between glycated protein and un-glycated protein, or between glycated protein and total protein, as an indication of the fraction of said protein which is glycated in said sample. In the assay, the contacting is performed under competitive binding conditions, and the first signal and second signal are distinguishable, e.g., spatially or distinguishably different signal (e.g., different wavelength of light emitted and/or different temporal emission properties).

In one aspect, the method comprises providing:
1. A first labeled binding member specific for:
   a. an unglycated protein (e.g., hemoglobin) or
   b. a peptide fragment thereof (of a.) specifically indicative of the unglycated protein;
   c. or total (glycated and unglycated) protein (e.g., glycated and unglycated hemoglobin);
   d. or a peptide fragment thereof (of c.) indicative of total (glycated and unglycated) protein; and
2. A second labeled specific binding member specific for the glycated form of the protein or peptide fragment (e.g., glycated hemoglobin (HbA1c) or a peptide thereof comprising a glycated amino acid).

The first and second binding members are contacted to a mixture comprising the protein of interest (e.g., hemoglobin obtained from a patient blood sample). In the hemoglobin example, humans generally have some amount of glycated hemoglobin and some amount of unglycated hemoglobin. As described elsewhere herein, the protein (of interest) can be pretreated with an endopeptidase to generate peptide fragments of the protein. In this case, the first and second binding members are contacted to a mixture comprising the peptide fragments.

The relative amounts of (i) glycated and (ii) total protein and unglycated can then be detected. In a competitive assay, the resulting mixture of binding members and protein or peptides is composed of (1) binding members bound to protein or peptide and (2) unbound excess binding members. The amount of excess binding members is then detected. The amount of unbound binding member is inversely proportional to the amount of target protein or peptide in the mixture. In some embodiments, the labeled, specific binding member specific for total hemoglobin protein specifically binds a peptide selected from the group consisting of $^8$KSAVTALWGKVNV$^{20}$, $^{11}$VTALW$^{15}$, $^{45}$FGDLSTP$^{51}$, $^{76}$AHLDNLKGTFAT$^{87}$, $^{49}$STPDAVMGNPKVKAHGKK-VLGA$^{70}$, and $^{122}$FTPPVQ$^{127}$.

The format of the assay can vary as desired. In some embodiments, the binding members (e.g., antibodies) are linked to a solid support, which can include but are not limited to beads or particles that can optionally be labeled. In some embodiments, lateral flow is applied to the mixture of binding members and proteins or peptides thereof from the sample to migrate the mixture to capture zones for the unbound binding members. For example, a first capture zone in a lateral flow path can comprise a peptide recognized by the first binding member, thereby immobilizing unbound first binding member. A second capture zone in the flow path can comprise a peptide recognized by the second binding member to immobilize the second binding member. The first and second capture zones can be in the same or different locations in the flow path.

In further embodiments, the mixture can further comprise additional binding members specific for protein (e.g., hemoglobin variants). As an example, the mixture can further comprise a third binding member specific for HbS and a fourth binding member specific for HbC. These binding members can also be linked to a solid support and are optionally labeled. Moreover, the third and fourth binding members can be immobilized in a lateral flow using peptides to which the respective binding members specifically bind. This will allow a user to further determine whether the sample is from a donor who carries a variant protein.

In some embodiments, the method includes lysing cells to release the protein (e.g., red blood cells containing the hemoglobin) and/or at least partially denaturing the protein (e.g., hemoglobin or albumin) and/or releasing the N-terminal peptide of the protein or relevant polypeptide of the protein using an endopeptidase (e.g., pepsin or endoproteinase GluC (S. aureus)) digestion.

In particular embodiments, the protein is human hemoglobin, e.g., hemoglobin A1c. In some embodiments, a peptide is an N-terminal peptide of human hemoglobin beta chain, e.g., 5-14, 5-11, 5-8, 5-7, 5, 6, 7, or 8 amino acid residues in length. In some embodiments, the protein is human serum albumin; a peptide is an N-terminal peptide of human serum albumin, e.g., a peptide 4-17, 4-16, 4-15, 4-14, 4-10, 4-8, 6-17, 6-16, 6-15, 6-14, 6-10, 6-8 amino acid residues in length. In some embodiments, a peptide includes human serum albumin Lue585, Lys525, Lys199, Lys439, or Lys281; a plurality of peptides are used which include peptides which separately include at 2, 3, 4, or 5 of albumin N-terminal amino acid, Leu585, Lys525, Lys199, Lys439, and Lys281 peptide, including each of the possible combinations. In some embodiments, peptide is cleaved (e.g., from hemoglobin or albumin in a sample) using an endopeptidase, e.g., pepsin or endopeptidase GluC; the peptide is a plurality of peptides, e.g., 2, 3, 4, 5, 6, 7, 8, 9, 10 or even more different peptides.

The label linked to the specific binding members can be, for example, fluorescent, Time Resolve Fluorescence (TRF), chemiluminescence, colormetric/absorbance or electrical/redox in nature. As noted above, the separate detection zones can be performed on a lateral flow assay device, where the device includes a detection zone with an immobilization site for hemoglobin A1C or corresponding peptide sequence and an immobilization site for un-glycated hemoglobin or corresponding peptide, and where signals are detected in separate zones. Additional detection zones can be included for variant detection. This can be one zone for all four variants or separate zones for each specific variant. In some embodiments, each specific binding member is linked to different copies of the same label (e.g., TRF) and are detected separately by capturing different binding members in different capture zones in the lateral flow device. In some embodiments, the signal detected from the label is phosphorescence.

For some embodiments, the assay reagent set also includes a buffer solution; the assay reagent set also includes an endopeptidase, e.g., trypsin, pepsin, Endopeptidase GluC, papain, or a prolyl endoptidase.

In certain embodiments, the first and second binding member signals are fluorescent signals or Time Resolve Fluorescence (TRF) signals. In some embodiments, the detecting is performed on a lateral flow assay device, where the device includes a detection zone with an immobilization site for binding members specific for glycated protein or peptide and an immobilization site for binding members specific for total protein or peptide (or un-glycated protein or peptide), and where signal corresponding to binding members specific glycated protein or peptide and signal corresponding to binding members specific for total protein or peptide (or un-glycated protein or peptide) are detected separately. In some embodiments, the assay device is as just specified and the immobilization site for binding members specific for glycated protein or peptide and said immobilization site for binding members specific for un-glycated protein or peptide are physically separate. In some embodiments, the assay device is as specified above and the immobilization site for glycated protein or peptide and the immobilization site for total protein or peptide (or un-glycated protein or peptide) are the same, and the first and second signals are different and thus are separately detected.

In particular embodiments, the first and second signals are from Luminescent Oxygen Channeling assay (LOCI) labels which include donor and acceptor labels.

In some embodiments using LOCI, the total protein or peptide (or unglycated version of the protein or peptide) and the glycated version of the peptide are immobilized or linked with donor LOCI labels, and the specific binding member specific for total protein or peptide (or un-glycated protein or peptide) and the specific binding member specific for glycated protein or peptide are attached with acceptor LOCI labels, e.g., where donor LOCI labels are or include beads (which may be coated) which include a plurality of donor LOCI label molecules and a plurality of the proteins or peptides are immobilized or immobilize on the surfaces of the beads (e.g., with covalent linkage to the bead or with specific binding such as biotin/streptavidin binding.

In other embodiments using LOCI, the total protein or peptide corresponding to total protein (or unglycated version of the peptide) and the glycated version of the peptide are immobilized with acceptor LOCI labels, and the specific binding member specific for total protein or peptide (or un-glycated protein or peptide), and the specific binding member specific for glycated protein or peptide are attached with donor LOCI labels.

In particular embodiments using LOCI, the assay is performed as a homogeneous assay or the assay is performed using a uniform suspension of fine particles (or exchange immunoassay) assay.

In certain embodiments, the coefficient of variation of the calculated glycated protein or peptide (e.g., HbA1c) for sample levels within the effective range of the assay system is less than 3.0, 2.7, 2.5, 2.3, 2.1, 2.0, 1.9, 1.8, 1.7, 1.6, 1.5, 1.4, 1.3, or 1.2%, based on a minimum of 20 replicate measurements.

A related aspect concerns a reagent set for a LOCI assay, including a glycated version of a particular protein or a glycated peptide derived therefrom glycated at a glycation site; a labeled, specific binding agent which includes a specific binding agent specific for a glycated version of the particular protein or specific for a glycated peptide derived therefrom linked with a first member of a first donor and acceptor LOCI label pair; a labeled, specific binding agent which includes a specific binding agent specific for an un-glycated version of the particular protein or specific for an un-glycated peptide derived therefrom linked with a first member of a second donor and acceptor LOCI label pair; and the second member of the first donor and acceptor LOCI label pair linked or linkable with the glycated version of the particular protein or glycated peptide derived therefrom; and the second member of the second donor and acceptor LOCI label pair linked or linkable with the un-glycated version of the particular protein or unglycated peptide derived therefrom. The first and second donor and acceptor LOCI label pairs may be the same or different.

In some embodiments, LOCI donor label is linked or linkable with the un-glycated protein or peptide and with the glycated version of said protein or peptide, e.g., where the LOCI donor label includes a bead which has a plurality of immobilized protein or peptide, or a plurality of binding sites for specific binding of protein or peptide.

In certain embodiments, the reagent set or components thereof are in an assay device; the components of the reagent set are combined with a sample containing the particular protein which can be glycated in vivo or a peptide derived therefrom which includes a glycation site.

For some embodiments, the assay reagent set also includes a buffer solution; the assay reagent set also includes an endopeptidase, e.g., trypsin, pepsin, Endopeptidase GluC, papain, or a prolyl endoptidase.

In some embodiments, the particular protein is human hemoglobin; the assay reagent set includes Hb A1c peptide; the reagent set includes an N-terminal peptide of human hemoglobin beta chain, e.g., 5-14, 5-11, 5-8, 5-7, 5, 6, 7, or 8 amino acid residues in length; the particular protein is human serum albumin; a peptide in the reagent set is an N-terminal peptide of human serum albumin, e.g., a peptide 4-17, 4-16, 4-15, 4-14, 4-10, 4-8, 6-17, 6-16, 6-15, 6-14, 6-10, 6-8 amino acid residues in length; a peptide in the reagent set includes human serum albumin Lue585, Lys525, Lys199, Lys439, or Lys281; the reagent set includes a plurality of peptides; the reagent set includes a plurality of peptides which separately include at least 2, 3, 4, or 5 of albumin N-terminal amino acid, Leu585, Lys525, Lys199, Lys439, and Lys281 peptide, including each of the possible combinations; the reagent kit includes one or more reagents as specified for the first aspect or as otherwise described herein for the present invention.

In some aspects a lateral flow device is provided (e.g., as described herein). In some embodiments, the lateral flow device comprises in flow communication in the following order: a sample intake area; an endopepsidase area (an area comprising an endopepsidase as described herein); optionally, a neutralization area (e.g., an area comprising reagents to neutralize solutions coming from the acidic endopepsidase area if needed, or optionally comprising reagents that bind or otherwise inactivate the endopepsidase); one or more reagent mixing area; one or more lateral flow strips; and an absorbant pad. In some embodiments, the at least one reagent mixing area comprises: (i) a labeled, specific binding member specific for total protein or a peptide corresponding to total protein or un-glycated protein or peptide, (ii) a labeled, specific binding member specific for glycated protein or peptide, and (iii) a non-sample-derived glycated version of said protein or peptide. In some embodiments, said protein is human hemoglobin. In some embodiments, said glycated protein is HbA1C. In some embodiments, the labeled, specific binding member specific for total protein specifically binds a peptide selected from the group consisting of $^{8}$KSAVTALWGKVNV$^{20}$, $^{11}$VTALW$^{15}$, $^{45}$FGDL-STP$^{51}$, $^{76}$AHLDNLKGTFAT$^{87}$, $^{49}$STPDAVMGNPK-VKAHGKKVLGA$^{70}$, and $^{122}$FTPPVQ$^{127}$. In some embodiments, the non-sample-derived glycated version of said protein or peptide is biotinylated and at least one of the one or more lateral flow strips comprise an immobilization zone comprising streptavidin. In some embodiments, at least one of the one or more lateral flow strips comprise separate immobilization zones as follow: an immobilization zone comprising a total protein or a peptide corresponding to total protein; an immobilization zone comprising the glycated protein or glycated peptide. In some embodiments, the same or different lateral flow strip comprises an immobilization zone comprising one or more protein isoform. In some embodiments, the protein isoforms include at least one of HbC, HbD Punjab, HbE, or HbS. In some embodiments, one lateral strip comprises separate immobilization zones as follows: an immobilization zone comprising a total protein or a peptide corresponding to total protein; an immobilization zone comprising the glycated protein or glycated peptide; and a second lateral flow strip comprises an immobilization zone comprising one or more protein isoform. In some embodiments, the glycated protein is a human protein; a lateral flow strip comprises the non-human target; and the reagent mixing area comprises a control labeled binding member that specifically binds the non-human target. In some embodiments, the labels are fluorescent or time resolve fluorescence (TRF) labels. In some embodiments, the labels of the binding members are the same label.

Additional embodiments will be apparent from the Detailed Description and from the claims.

DETAILED DESCRIPTION OF THE INVENTION

Figure 1:
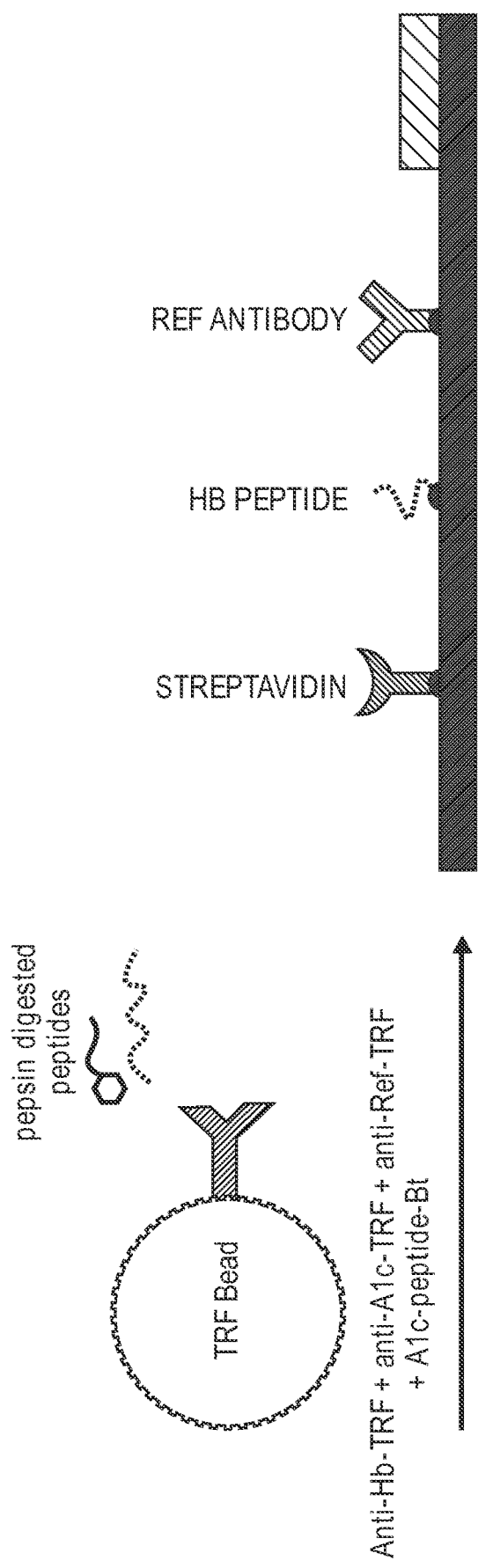
FIG. 1 is a schematic representation of a ratiometric A1c assay setup. A mixture of TRF-functionalized anti-Hb, anti-A1c and Reference (control labeled binding member) beads is mixed with pepsin-digested blood sample and a biotinylated synthetic A1c peptide. The reaction mixture is moved by capillary action into nitrocellulose membrane striped with streptavidin (for A1c detection), synthetic Hb peptide (for Hb detection) and a reference antibody. The released Hb and A1c peptides compete for the appropriate zone resulting in signal reduction with increasing concentration of peptides. The reference zone provides signal to normalize for flow irregularities, membrane imperfections, and variations in reagent concentrations. Depending on standard curves, the analytical signals can be obtained either by dividing any of the analyte zone (Hb, A1c) signal by the reference zone signal or by dividing analyte zones by each other.

The present invention is directed to assay methods detecting levels of particular glycated proteins. Such methods are useful, for example, for monitoring the average levels of blood glucose in an individual (usually human, but the methods are also applicable to other animals, particularly other mammals). While numerous methods are available for determining glucose levels at a particular time point, it is also useful to be able to monitor average levels over time. It has been found that the glycation levels of certain proteins, particularly hemoglobin and serum albumin, correlates strongly with average glucose levels over a preceding time period corresponding to the average lifetime of the particular protein in the body. Because of the approximate 90-120 day lifetime of hemoglobin in the blood, glycated hemoglobin is useful as an indicator of average glucose levels over the preceding 2-3 months, with greater weighting on the prior one month, while albumin can be used as an indicator of glucose levels over the preceding 1-3 weeks. Because hemoglobin variants can have different lifespans in the blood, it can be helpful for assay interpretation to indicate whether the patient tested carries one or more hemoglobin variant forms. Quantitative or semi-quantitative information about the quantity of hemoglobin isoform can indicate that the patient is heterozygous or homozygous for a particular variant and a physician can take that into account when assessing the assay results.

Thus, the present methods may be used, for example, to quantitate levels of glycated hemoglobin, but can also be used for quantitating levels of glycated non-hemoglobin proteins, e.g., albumin. In most cases, the present assays are configured to provide relative amounts of glycated protein to non-glycated protein, for a particular protein of interest.

The following description focuses on determination of glycated hemoglobin, but it should be recognized the methods also apply to detection of other glycated proteins with replacement of binding molecules specific for hemoglobin with binding molecules specific for the other desired protein together with the other corresponding materials and empirically selected process adjustments. In the assays, while full-length proteins or polypeptides may be used, in many cases it is useful to use short peptides, often about 4-20 amino acid residues in length. Such peptides may be cleaved from the full-length polypeptide using an endopeptidase having suitable cleavage site specificity.

In some aspects, determination of percent glycated hemoglobin (% HbA1C) with hemoglobin variant detection is provided. In the assays, while full-length proteins or polypeptides may be used, in some cases it is useful to use short peptides, often about 4-20 amino acid residues in length. Such peptides may be cleaved from the full-length polypeptide using an endopeptidase having suitable cleavage site specificity. Detection of peptides (polypeptide fragments) can improve precision and accuracy of the assay.

A. Hemoglobin Assay Configurations

Assay formats described herein are suitable for use with various labels and detection schemed including but not limited to: fluorescent, Time Resolve Fluorescence (TRF) chemiluminescence, colorimetric/absorbance or electrochemical. In order to achieve multiplexed results (multiple results on one test), this assay configuration can be performed using a lateral flow configuration, with separate binding/detection zones for non-glycated Hb (or Total Hb) and for glycated Hb (HbA1C).

Two different configurations of the glycated hemoglobin assay have been developed, and are adaptable to other glycated protein assays. The first utilizes a luminescent label such as a fluorescent, phosphorescent, or Time Resolve Fluorescence (TRF) label. This assay configuration can, for example, be performed using a lateral flow configuration, usually with separate binding/detection zones for Hb and for glycated Hb (HbA1C), although multiplexing may be used. TRF signal can be detected by detecting phosphorescence. In some embodiments, the TRF signal is detected such that fluorescence or auto-fluorescence is minimized. The measurement of phosphorescence may be achieved by intermittent optical excitation at one wavelength (for example in the ultra-violet region) and subsequent measurement of the decaying luminescence signal at another wavelength (usually in the visible region). In this way phosphorescence, which has a relatively long decay time (typically anywhere in the region of microseconds to seconds), may be distinguished from fluorescence, which has a relatively short decay time (e.g. typically less than 1 micro-second).

Examples of detection of TRF signal are described in, e.g., PCT/GB2012/051645. For example, PCT/GB2012/051645 describes an apparatus for use in measuring a luminescent property of a sample, the apparatus comprising: an excitation light source for emitting radiation to excite said sample, under the control of a control signal; a signal source for generating said control signal for modulating an intensity of said emitted radiation, said control signal having a first component at a first frequency having a period that is less than, or of the same order as, an expected characteristic time constant of said luminescent property, and a second component at a second frequency having a period that is greater than said expected characteristic time constant of said luminescent property; a photodetector for receiving radiation luminesced from said sample as a result of said excitation, and for generating a detection signal representing an intensity of said received radiation; and a demodulator for demodulating said detection signal whereby to produce a signal representing said luminescent property of said sample.

Other configurations may also be used. The second uses a proximity label method, usually Luminescent Oxygen Channeling Assay (LOCI), which can be performed, for example, using a split sample arrangement or using multiplexing. Each of these configurations is described in greater detail below.

1. Sample Treatment

For determining the level of glycated hemoglobin, in most cases a (human) blood sample is used. The blood sample or resuspended cells are contacted with a red blood cell lysing agent (e.g., a suitable lysing detergent or detergent combination) to release the hemoglobin from the red blood cells. In many cases, the sample is contacted with the red blood cell lysing agent prior to being added to the assay device, e.g., as a sample pretreatment. However, the lysing agent may instead be included in an assay device. Numerous such red blood cell lysing agents are known and may be used, for example, various detergent-containing compositions. Suitable red blood cell lysing agents include, for example, Triton X-100 and Igepal CA-630, and others are known to those of skill in the art and may be used.

In addition to lysis of red blood cells, the sample treatment can include treatment to denature the native hemoglobin, e.g., to dissociate the hemoglobin tetramer, and can further denature the beta chains. For example, it can be beneficial to treat the hemoglobin at low pH (e.g., about pH 4 or 1-3) to better expose the beta-chain N-terminal peptide for cleavage to release N-terminal peptide. In the case of pepsin cleavage, such acidic conditions (or even more acidic conditions) are also appropriate for pepsin activity.

In addition, the treatment can include dilution of the sample to provide appropriate reduced concentrations of Hb for detection. The dilution is selected to be compatible with the sensitivity and dynamic range of the assay to be used.

For other proteins, sample treatment will depend on the protein of interest. While hemoglobin is an internal component of red blood cells, other glycatable proteins are extracellular in the blood (e.g., human serum albumin), embedded in or attached to cell walls, or intracellular in other types of cells. For example, for extracellular proteins it will often be desirable to remove cellular components from the sample, such as by filtration or other cell removal methods. Likewise, for cell membrane proteins embedded in or attached to membranes, it is often useful to release the protein from the membrane, e.g., using suitable detergents.

As with hemoglobin, it can be useful to denature multicomponent proteins and/or to at least partially denature protein secondary and/or tertiary structure to make binding or cleavage sites more accessible. The need for such denaturations can be readily determined for each particular protein, and appropriate denaturing agents and/or conditions selected.

2. Hemoglobin Peptide Cleavage

As indicated above, the present assays can be conducted using either intact proteins or polypeptides, or with short peptides derived from the protein. While the assay can be performed using intact hemoglobin (usually denatured to dissociate the subunits), detection of the glycated peptide fragment instead of the intact protein is usually used in the present methods.

Hemoglobin is primarily glycated on the N-terminal beta-chain valine residue (usually on only one of the two beta-chains in the native tetrameric structure). Thus, the sample treatment can also include cleavage of the hemoglobin to provide a peptide fragment which includes the N-terminal valine. This can be accomplished using a suitable peptidase(s), for example, an endopeptidase, e.g., pepsin or endoproteinase GluC, digestion. Depending on the peptidase(s) selected and digestion conditions, in some embodiments the resulting N-terminal beta chain peptide will be about 5-11 residues in length.

When using pepsin for cleavage, generally the solution is made acidic, e.g., to about pH 1.1-4.5 (often about pH 1.2-2.0) and the cleavage is allowed to proceed for an empirically-determined suitable time. For pepsin, commonly a suitable digestion time will be about 0.1 to 60 minutes at 37° C. and in certain embodiment 0.3-3.0 minutes. The pepsin can then be inactivated through denaturation by raising the pH to about pH 8.0.

The endopeptidase can be contacted to the sample as a liquid or solid formulation. For example, the endopeptidase can be formulated as a lyophilized or otherwise dry composition that is readily dissolved when contacted by a liquid sample. Following endopeptidase digestion, the resulting solution can be contacted with a buffer to raise the pH of the solution, e.g., to between pH 6-8, e.g., 7.2-7.8, e.g., 7.4.

3. Hemoglobin Isoform Detection

The present methods have been found to enable a significant advance by providing multiplexed detection and measurement of multiple hemoglobin isoforms, either as intact proteins (or intact sub-units) or by detecting characteristic isoform peptides (distinguishable peptides which include the respective mutated residue). In some embodiments, a characteristic isoform peptide includes the respective mutated residues: HbC (E6K), HbS (E6V), HbE (E26K), and HbD Punjab (E121Q). Reference to these isoforms of hemoglobin are as standard in the field. Reference herein to HbD without further polymorphism identification shall mean HbD Punjab (HbD Los Angeles).

The most frequently-occurring hemoglobin is HbA (normal adult Hb), with variant isoforms HbC, HbD, HbE, and HbS occurring at various frequencies in the human population. These listed variant isoforms all involve mutations in the beta chain. The isoforms of interest can be detected in the present glycated hemoglobin assays using antibodies with good specificity for the respective isoforms (or more advantageously having good specificity for characteristic isoform peptides) to form the complexes (e.g., for capture and labeling to form the detectable complex for TRF detection). The various isoforms can be detected in a single multiplexed zone or in different zones. Antibody specificity and hemoglobin variants are described, for example, in U.S. Pat. No. 8,603,828 B2. Monoclonal antibodies that detect total hemoglobin can be selected that bind to an epitope common to HbA and hemoglobin variants. Monoclonal antibodies that specifically detect unglycated hemoglobin can be selected that bind a hemoglobin peptide that has a potential glycation site but that is not glycated. Exemplary peptides useful for raising antibodies capable of accurately detecting total hemoglobin protein include, e.g., $^{8}$KSAVTALWGKVNV$^{20}$, $^{11}$VTALW$^{15}$, $^{45}$FGDLSTP$^{51}$, $^{76}$AHLDNLKGTFAT$^{87}$, $^{49}$STPDAVMGNPKVKAHGKKVLGA$^{70}$, $^{122}$FTPPVQ$^{127}$.

The isoform detection described above provides detection without interference by HbF (α2γ2) because the respective beta-chains (beta chain peptides) are not present in HbF and appropriately isoform-specific will not bind HbF protein or peptides.

It has also been discovered that pepsin digestion as used for release of A1c peptide also releases suitable characteristic isoform peptides for HbC, HbD Punjab, HbE, and HbS. As a result, a single digestion suitable for any or all of HbA1c, HbC, HbD, HbD, and HbS can be carried out in a single pepsin digestion reaction. This can be performed within an assay device, with subsequent isoform detection based on specific binding with characteristic isoform peptides.

The digestion for A1c will also release corresponding N-terminal peptides from the other isoforms. As a result, the A1c/non-glycated peptide ratio determination will include the other Hb isoforms in the ratio determination.

Other endopeptidases can also be used once it is confirmed the particular peptidase releases a suitable peptide(s). When using such other peptidase, it will usually be desirable to terminate the digestion reaction at some point. Such termination can be accomplished using a corresponding inhibitor or other method appropriate for the endopeptidase of interest. In some cases, it may be desirable to utilize two or more different endopeptidases, usually separately.

4. Lateral Flow HbA1c Assay

As indicated above, the assay can be performed using a lateral flow configuration, with either undigested Hb or with one or more peptide from the beta chain. The methods can be performed as a competitive assay involving determination of total Hb and glycated Hb, thereby providing the ratio (which may be expressed as a percentage) of HbA1C to total Hb, although it is also possible to construct a non-competitive assay. Thus, the assay includes at least two detections: 1) determination of total Hb (or alternatively non-glycated Hb); and 2) determination of glycated Hb. Thus, in some cases, the assay determines the level of non-glycated Hb and glycated Hb, and the total Hb is then determined as the sum of the non-glycated Hb and glycated Hb. This can be of particular use to improve precision when both the non-glycated Hb and glycated Hb values are generated with the same type of assay, such that imprecision that occurs in one measurement can "cancel out" or reduce a similar error in the other measurement, for example when using a ratio such as the following.

The % HbA1C can then be calculated as:

% HbA1C=[HbA1C]/([HbA1C+Non-glycated Hb]× 100=[HbA1C]/[Total Hb]×100

The description in this section focuses on the competitive assay using the competitor peptide. In some embodiments, for the total Hb determination, a peptide cleaved from sample Hb (sample) and a non-glycated N-terminal peptide competitor (an exogenous peptide not from the sample, often synthetic) are competing for binding with a labeled specific binding agent for a non-glycated Hb peptide, e.g., an anti-Hb peptide antibody. In some embodiments, the peptide consists of or comprises amino acids 49-70 of Hb, but in any case is a peptide that comprises all or part of the epitope recognized by the binding agent for non-glycated Hb. The binding agent can be labeled, linked to a bead or particle, or both. In some embodiments, the binding agent is immobilized or can be captured in a detection zone (e.g., using biotin-streptavidin binding or by specific binding of the binding member to an immobilized peptide). The two peptides (one from the sample and one being the competitor peptide) compete for binding to the specific binding agent and the amount of binding of the sample peptide or the competitor peptide to the specific binding agent is detected. An aspect of this is illustrated in FIG. 1.

For example, in some embodiments, the endopeptidase-treated and neutralized sample is contacted with a labeled specific binding member specific for a peptide representative of total protein and the resulting mixture is subsequently contacted to an immobilized peptide that competes for binding to the specific binding member. Binding to the immobilized peptide is inversely proportional to the amount of target peptide in the sample. The signal detected is inversely related to the level of total Hb in the sample.

Similarly, in the same reaction, for the HbA1C determination, N-terminal peptide cleaved from sample HbA1C (sample) and a glycated N-terminal peptide (not from the sample, usually synthetic) are competing for binding with a labeled specific binding agent (e.g., antibody) for the HbA1C N-terminal peptide. The binding agent can be immobilized or can be captured in a detection zone (e.g., using biotin-streptavidin binding). The two peptides compete for binding to the specific binding agent. The signal detected is inversely related to the level of non-glycated Hb in the sample.

For example, in some embodiments, the endopeptidase-treated and neutralized sample is contacted with a labeled specific binding member specific for a peptide representative of glycated Hb (e.g., A1c) and the resulting mixture is subsequently contacted to an A1c peptide that competes for binding to the specific binding member. The A1c peptide can be immobilized initially or in another embodiment, the A1c peptide can be biotinylated. In the latter case, A1c in the sample competes with the competitor A1c peptide for binding to the binding member and subsequently the competitor biotinylated A1c peptide is captured in a zone comprising immobilized streptavidin, thereby capturing the biotinylated competitor A1c and any specific binding member bound to the biotinylated competitor A1c. Binding to the immobilized peptide is inversely proportional to the amount of target peptide in the sample. The signal detected is inversely related to the level of A1c in the sample.

The detection zones for the non-glycated Hb and HbA1C are different in assays in which the same label is used for both detections but the detection zones may be the same in assays in which different labels are used which provide distinguishable signals.

In aspects where Hb variants are to be detected, the sample can be contacted with labeled binding members specific for the variants (e.g., a different specific binding member for each variant to be detected) and then contacted to a competitor peptide for each variant to be detected. As with the assays discussed above, in some embodiments, the competitor peptide for each variant can be immobilized and binding of the labeled specific binding member to the competitor peptide is inversely proportional to the amount of the variant in the sample. The labeled binding members specific for the variants can be captured in the same lateral flow strip as where the total and glycated protein is detected, or alternatively can be detected in a separate lateral flow strip. See, e.g., FIGS. 2 and 3.

In some embodiments, the mixing occurs in a liquid phase (e.g., in a microfluidic channel, not in a lateral flow strip or pad) and is delivered directly from the liquid phase to a lateral flow strip. This aspect avoids some problems that can occur in standard lateral flow assays where mixing occurs in a "dry phase" (i.e., in a pad or membrane) where junctions between pads and membranes can interfere with particle movement, resulting in some additional degree of imprecision.

In some embodiments, control binding reactions can also be performed and can be used to normalize signal from the binding reactions described above. For example, in some embodiments, the binding member mixture can further comprise a control labeled binding member that specifically binds a target likely not in the sample. As an example, the control labeled binding member (e.g., antibody) can have binding specificity for a protein from a different species (e.g., a goat IgG). The control labeled binding member can be submitted to lateral flow with the rest of the solution and then be captured in a zone comprising a protein that specifically binds the control labeled binding member (e.g., an anti-goat IgG). The amount of binding should remain fairly constant but will vary depending on variables in the assay other than specific binding affinity. The signal generated from the control can then be used to normalize other target signals thereby reducing variation in the assay.

5. LOCI HbA1c Assay

It has been discovered that an HbA1c assay can be effectively designed using Luminescent Oxygen Channeling Assay (LOCI). An effective configuration is in competitive assay format. In many cases, the specific binding agent is contacted first with the cleavage peptide and then with the synthetic peptide, but the order can be reversed or the contact may be at the same time.

Thus, in the competitive LOCI assay, components can include a synthetic or purified Hb peptide linked with a LOCI donor or acceptor label (e.g., either bound to the label or can be bound to the label, such as by using a streptavidin/biotin pair), and a similar synthetic or purified A1c peptide. There is also an anti-Hb peptide and an anti-HbA1C peptide antibody (or other specific binding agent), each linked with the other of a LOCI donor or acceptor label pair.

In one configuration, the sample is split following sample treatment such that the levels of Hb peptide and HbA1C peptide respectively are determined in separate spaces or locations, e.g., in separate solution volumes. As an example, sample can be deposited in separate wells, or can flow into separate flow channels.

As an alternative to splitting the sample, the assay may be multiplexed, e.g., by use of LOCI acceptor labels which emit light at distinguishably different wavelengths and/or at distinguishably different times. A number of such acceptors are known and may be used.

In some embodiments, the basic assay using A1c peptide involves use of and un-glycated N-terminal peptide and a glycated N-terminal peptide. The un-glycated N-terminal peptide and the glycated N-terminal peptide may be used in separate competitive binding reactions, or may be used in a single binding reaction in conjunction with multiplexing. The reaction for glycated peptide will be described; the reaction for the un-glycated peptide is substantially the same except that it involves antibody specific for the unglycated peptide. In some embodiments, the peptide is linked with biotin, but may instead be linked directly to the LOCI donor bead. The binding mixture also includes anti-HbA1C peptide linked with LOCI acceptor label. (Note, the other reaction will involve anti-Hb N-terminal peptide.) These reagents and sample containing cleaved glycated N-terminal peptide (HbA1C peptide) are brought together, and competitive binding of the cleaved N-terminal peptide and the peptide linkable or linked with the LOCI donor label is allowed to occur. The result is that the antibody-acceptor label conjugate will be bound to cleaved peptide and peptide linked or linkable to the donor label in relative proportions corresponding to their respective numbers in the binding reaction mixture.

When the LOCI donor label is contacted with light of a wavelength appropriate for that label, the donor label generates singlet oxygen. Because singlet oxygen has a very short lifetime in aqueous medium, it will only elicit light emission from the acceptor label if the distance between donor and acceptor labels is short, i.e., if peptide linked with the donor label has bound to it an antibody-acceptor label conjugate. For antibody-acceptor label conjugate which is bound with peptide from the sample, no light emission will occur because there is not closely linked LOCI donor label (i.e., singlet oxygen generator).

As a result, when the completed competitive binding mixture is illuminated with light of a wavelength suitable for generating singlet oxygen from the LOCI donor label, the intensity of the emitted light signal will be inversely related to the concentration of the cleaved peptide in the binding reaction mixture. Thus, the higher to concentration of the cleaved N-terminal peptide, the smaller the resulting signal will be, and conversely, the lower the concentration of cleaved N-terminal peptide, the larger the resulting signal will be. The signal corresponding to the glycated peptide and the signal corresponding to the un-glycated peptide are correlated with the respective relative peptide concentrations. The fraction of peptide which is glycated can then be calculated as the ratio of glycated peptide to total peptide as:

$$\text{Fraction glycated}=[\text{gHb}]/([\text{gHb}+\text{Hb}]=[\text{gHb}]/([\text{total Hb}]$$

In some cases, the assay using LOCI provides high precision, giving results for the calculated HbA1c percentage with a CV of less than 3.0, 2.7, 2.5, 2.3, 2.1, 2.0, 1.9, 1.8, 1.7, 1.6, or 1.5%, based on a minimum of 20 replicates.

6. HbA1c Assay Examples

Assays have been performed using TRF label in lateral flow format, and using competitive LOCI.

Pepsin Digestion and Assay Preparation

Conditions for peptidase digestion can be varied significantly. An example of pepsin conditions can be found in, Thomas et al., *Reg. Toxicol Pharmacol* 39 (2004) 87-98. In view of the potential variation, varying conditions were tested for releasing Hb N-terminal peptide, including the following:

1. Hb (both A1c and unglycated Hb) is diluted to 5 mg/mL (3×).
2. 1 mg/ml pepsin is prepared in 84 mM HCl, 35 mM NaCl at pH 1.3 (simulated gastric fluid—SGF).
3. 100 uL of SGF is dispensed into 12 tubes and heated to 37 C.
4. To 6 tubes was added 5 uL of total Hb (5 mg/mL), last tube has no pepsin.
5. To another 6 tubes added 5 uL of A1c (5 mg/mL), last tube has no pepsin.
6. Both Hb and A1c tubes are taken out at 5, 10, 20, 30, and 60 min quenched with 35 uL of 0.2M NaHCO3 pH11 and then heated at 85 C for 10 min.

TRF Assay Example

For the test assay, small scale digestion is used with SGF. In this digest protocol, 2 µl of digest sample ([Hb]=180 µg/ml) is added to 149 µl SGF (containing pepsin), pH 1.3 at 37 degrees C. Digestion is allowed to proceed for 1 min, then is quenched by adding 50 µl 0.2M NaHCO3 pH11 (also containing fructosylvaline at 5 mg/ml) giving a final [Hb] =1.8 µg/ml.

For the actual assay, 16 µl of the digest was combined with 2 µl of TRF-antipeptide antibody (at 5 µg/ml) and 2 µl of biotinylated peptide (at 20 µg/ml).

The mixture is applied to the assay strip bearing a streptavidin strip. The antibody competitively binds both peptide from the digest and the biotinylated peptide, but only the biotinylated peptide-Ab complexes will be immobilized at the streptavidin stripe (capture zone of the assay strip). The assay can be run to give quantitative glycated peptide results, or can be run with both glycated and unglycated peptides to give ratio (e.g., percentage) results. When both glycated and unglycated peptides are assayed, they may be run separately (e.g., using a single sample and two different strips) or together with multiplexing (e.g., with labels which emit at distinguishably different wavelengths and/or with distinguishably different temporal characteristics or by capturing at different locations of the assay strip).

Ratiometric Measurement and Normalization Results in Reduced Assay Variation

A ratiometric assay was designed in which one lane was reserved for an A1c competitive assay and another comprised anti-Goat antibody to which goat antibody-modified TRF particles admixed with anti-A1c Ab modified would bind to form a reference line. The strip used in this assay contained two lines: streptavidin and anti-Goat antibody. The A1c assay was run by mixing anti-A1c-TRF beads with biotinylated A1c peptide and inhibiting the binding with digested A1c calibrator on the streptavidin line. Anti-Goat Ab was striped onto the second line and served as a constant reference. The anti-A1c-TRF and Goat-TRF beads were mixed and their relative concentrations were adjusted to give approximately equal signals at zero inhibition.

Figure 4:
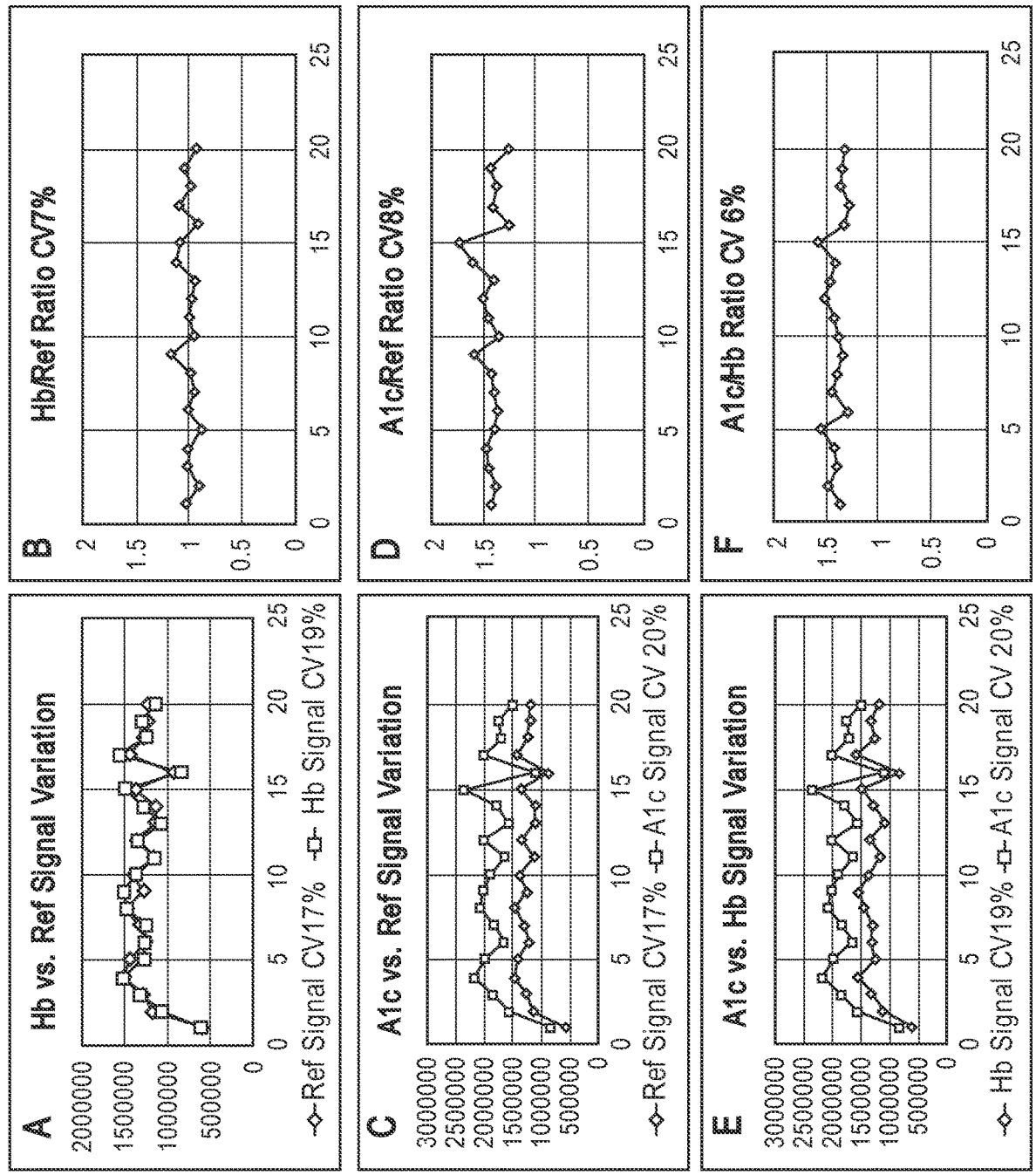
FIG. 4 provides a selection of data demonstrating advantages of ratiometric measurement of hemoglobin and A1c. The different graphs show the advantage of various normalizations to reduce variation within the assay.

FIG. 4 provides data from the above-described assay. When total Hb and Ref signal are measured independently, variation was measured at 17 and 19% CV, respectively (FIG. 4, A and B). Division of Hb signal by Reference signal reduced CV to 7%; (FIG. 4, C and D). When A1c and Ref signal were measured independently, variation was measured at 20 and 17% CV, respectively. Division of Hb signal by Reference signal reduced CV to 8%; (FIG. 4, E and F). When A1c and Hb signals are measured independently, variation was measured at 20 and 19% CV, respectively. Division of Hb signal by Reference signal reduced CV to 6%.

Detection of Hb Variants (Isoforms)

Figure 2:
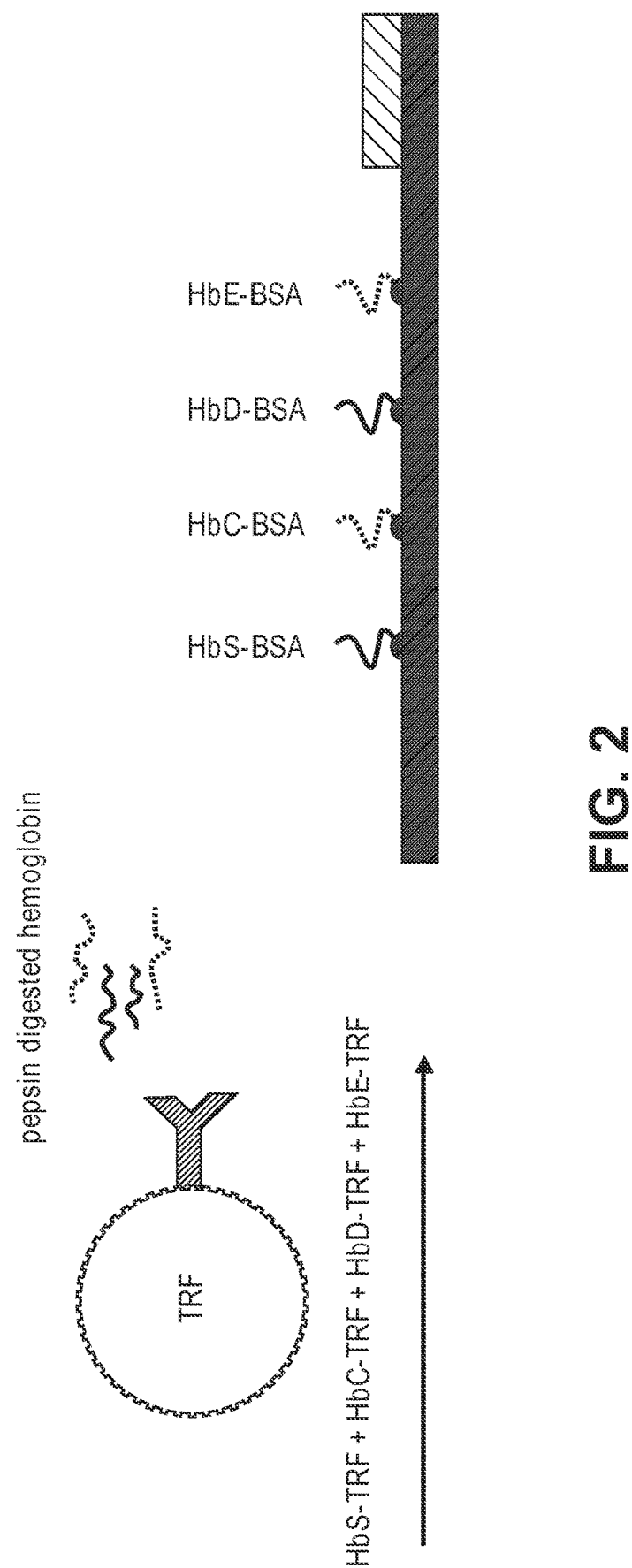
FIG. 2 is a schematic representation of a hemoglobin variant detection assay setup, referred to here as "SCDE" for the four variants detected in this particular configuration. A mixture of TRF-functionalized anti-HbS, anti-HbC, anti-HbD, and anti-HbE beads is mixed with pepsin-digested blood sample. The reaction mixture is moved by capillary action into nitrocellulose membrane striped with synthetic SCDE peptide conjugates. If one of SCDE peptides is present in a sample, a competition at an appropriate zone will take place leading to reduced binding. The presence/absence of each isoform is determined by a certain reduction in signal level.
Figure 3:
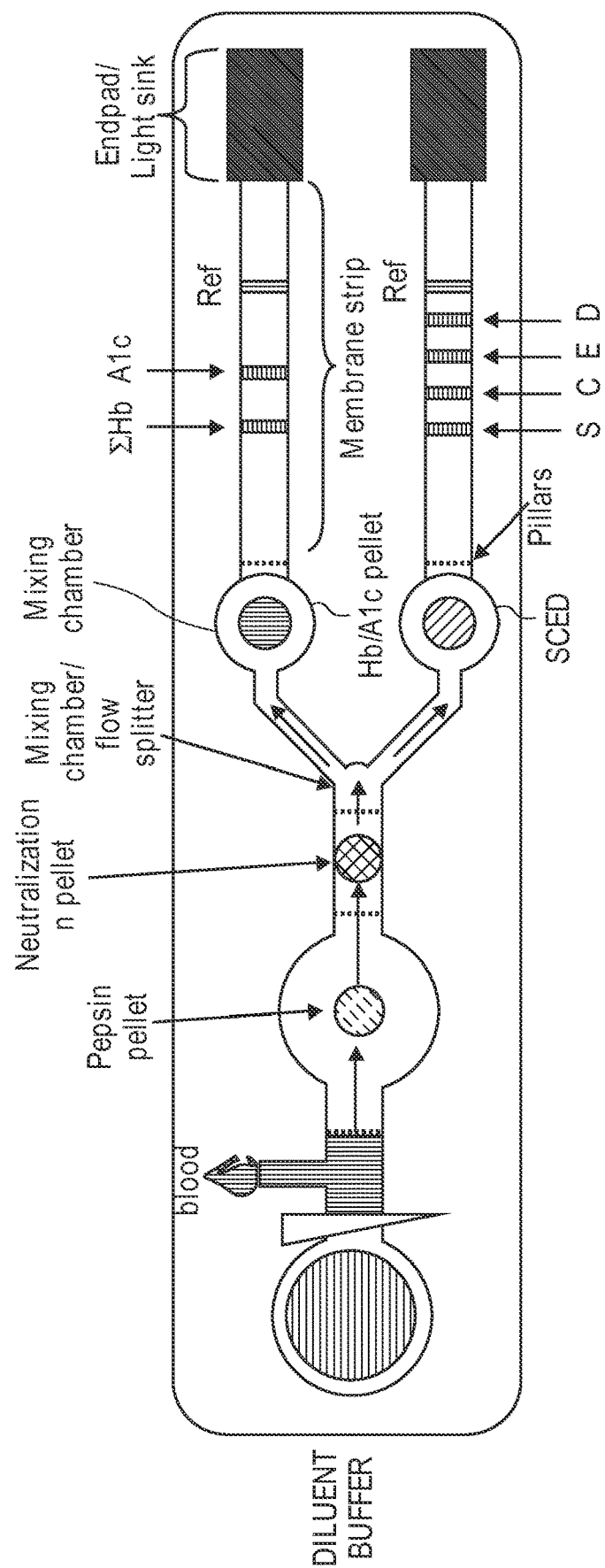
FIG. 3 is a schematic representation of a detection assay configuration for detecting both A1C levels and whether the patient carries a hemoglobin variant. A diluent buffer reservoir provides diluent that is mixed with a blood sample. The mixture is moved (e.g., by vacuum or capillary action for example) in a channel to a chamber containing an endopepsidase (depicted as "pepsin" where blood proteins are rendered into peptides. The resulting peptide mixture is moved to a neutralization region (neutralizing endopepsidase activity, e.g., changing the solution pH to inactivate an acid-active endopepsidase such as pepsin) and then mixed with the binding members (e.g., TRF-functionalized anti-Hb, anti-A1c and Reference (control labeled binding member) beads) and competitor A1c (e.g., a biotinylated synthetic A1c peptide) in liquid phase. The mixture can optionally be split (or not) into different lateral flow strips, one of which detects hemoglobin and A1c and reference levels and one of which detects hemoglobin variant proteins, if present. An end pad absorbs liquid from the reaction thereby drawing the liquid across the strip(s).

Patient samples known to contain Hb isoforms were digested with pepsin in simulated gastric fluid (SGF) at 37° C. The digested sample was diluted to a total of 500× with assay diluent. Eighteen microliters of the above sample was added to a lyophilized pellet containing four SCED bead types. The reaction mixture was run up an immunochromatographic membrane striped with HbS, HbC, HbD, and HbE peptides (FIG. 2). The strip was then read directly in a TRF reader. Table 1 shows percent signal remaining on each zone of the strip relative to average signal HbAA non-isoformic negative control, demonstrating that different isoforms can be detected by the assay.

TABLE 1

| Sample | % Variant | [Hb] g/dL | % of Ave HbE | % of Ave HbD | % of Ave HbC | % of Ave HbS |
|---|---|---|---|---|---|---|
| HbAA | NA | 24 | 93% | 111% | 107% | 91% |
| HbD | 40% | 12.8 | 97% | 6% | 100% | 92% |
| HbD | 41% | 14.3 | 104% | 6% | 103% | 85% |
| HbD | 41% | 15 | 85% | 5% | 90% | 78% |
| HbD | 41% | 15.2 | 89% | 5% | 95% | 81% |
| HbD | 40% | 14.3 | 87% | 4% | 95% | 77% |
| HbD | 26% | 6.5 | 115% | 9% | 100% | 81% |
| HbS | 39% | 16.7 | 115% | 103% | 101% | 22% |
| HbS | 39% | 10.8 | 102% | 106% | 100% | 21% |
| HbS | 39% | 14.1 | 75% | 83% | 90% | 28% |
| HbS | 36% | 11.5 | 89% | 93% | 97% | 21% |
| HbS | 41% | 11.6 | 96% | 106% | 99% | 18% |
| HbC | 36% | 14.9 | 125% | 121% | 0% | 92% |
| HbC | 35% | 14.4 | 93% | 100% | 8% | 106% |
| HbE | 25% | 10.7 | 20% | 86% | 82% | 93% |
| HbE | 25% | 13.1 | 30% | 106% | 102% | 118% |

LOCI Assay Example

Conducting the assay as a LOCI assay using Hb A1c peptide, high precision results were obtained. In the following "Acceptor" refers to the LOCI acceptor label, and "Donor" refers to the LOCI donor label. The LOCI assay example used the same digestion as the TRF example. To perform the assay, 14 µl of the digest was combined with 2 µl of the Acceptor-antiPeptide antibody complex solution at 200 µg/ml, 2 µl of biotinylated peptide solution at 2 µg/ml, and 2 µl of streptavidin-Donor conjugate. The mixture was held for one hour in the dark, and then the signal was read. As with the TRF example, the assay for glycated peptide and for un-glycated peptide can be run so the signals are in separate locations, or the signal can be multiplexed.

7. Alternative Assay Configurations

In addition to the general assay configuration described, some of the present assays can be configured in other ways.

In some aspects, again illustrating the configurations with HbA1C though the configuration is also applicable to other glycated proteins, an assay in lateral flow or in LOCI format can be carried out using a first antibody against the peptide of interest, e.g., the HbA1C peptide from the patient sample, and a synthetic competitor A1c peptide. For lateral flow, synthetic A1c peptide is immobilized or free but immobilizable (e.g., using a streptavidin-biotin pair, for example where the synthetic A1c peptide is linked to biotin and can be immobilized at a location via binding to streptavidin) at a first location on the assay strip. As a result, synthetic A1c peptide binds with the first antibody and is immobilized or immoblilzable at the first location. Thus, with the competitive binding between the synthetic A1c peptide and cleaved A1c peptide from the patient sample, anti-peptide antibody-labeled conjugate which is not bound with cleaved peptide from the patient sample will bind the immobilized or immobilizable synthetic A1c peptide. The label immobilized with the synthetic peptide provides a signal inversely related to the concentration of the A1c peptide in the sample. Antibody-label conjugate which is bound with cleaved peptide from the patient sample will not bind at the first location because it does not bear a binding moiety (such as biotin).

In some embodiments, a second antibody specific for HbA1C is also provided. In this embodiment, the second antibody, with bound cleaved peptide from the patient sample, will bind at a second location. If the concentration of second antibody is titrated such that essentially all of the second antibody is bound with cleaved peptide from the patient sample, the signal at the second location will be related to the concentration of cleaved peptide in the sample, which can therefore be correlated with the concentration of HbA1C in the original sample. In this format, the second location acts as a check on the competitive binding and the signal at the first location.

Another alternative involves use of an anti-glycated peptide antibody and an antibody against the full protein or against a peptide correlated with full protein. It also involves digestion of the protein to release the particular glycated peptide, e.g., an N-terminal peptide. If an antibody against full protein is used, in some embodiments digestion is only partial, while retaining critical epitope structure for recognition by the anti-protein antibody. If additional digestion is used, an antibody against a second peptide correlated with total protein is suitable. For lateral flow format, digestion solution containing cleaved glycated peptide and partially digested protein (or other peptide correlated with total protein) is applied to the strip, which has immobilized synthetic peptide (or streptavidin or other binding member for immobilizing synthetic peptide) at a first location. The cleaved glycated peptide from the patient sample competes for binding with immobilizable (e.g., using streptavidin/biotin pair) or immobilized synthetic peptide. As a result, the binding at the first location results in signal which is related to the inverse of the cleaved peptide concentration in the sample. A second location contains an immobilization agent for the antibody-protein (or antibody-second peptide) conjugate.

Assays using LOCI can also be designed for dual determinations involving glycated peptide and total protein or peptide correlated with total protein (for a particular protein). In such assays, the components include one of a LOCI label pair linked with or linkable with synthetic glycated peptide and the other of the LOCI label pair linked with antibody against the peptide. Cleaved peptide competes with synthetic peptide for binding to the labeled antibody. As described previously, the signal is related to the inverse of the cleaved (sample) peptide concentration. The detection of glycated peptide is paired with detection of protein or peptide correlated with total protein. The respective detections can be conducted in separate volumes or in single volume with multiplexing providing distinguishable signals.

B. Albumin Assay Configurations

Another protein subject to non-enzymatic glycation in vivo is human serum albumin, which has a serum half life of about 20 days. Determination of glycation level of albumin has been proposed as a measure useful in diabetes management.

While the different configurations as described for the hemoglobin A1c assay can be used for glycated albumin, the LOCI method is beneficial for this application. As before, this method uses LOCI, and can be performed, for example, using a split sample arrangement or using multiplexing. It has been reported albumin is principally glycated naturally at four sites, with the N-terminus predominant.

The assay can be structured to utilize one or more of the natural glycation sites, and can utilize intact albumin or peptide fragments with natural glycation sites, for example, lysine residues which are accessible for glycation. In some cases, the glycation sites selected will include the N-terminus and/or one or more of Lys525, Lys199, Lys439, and Lys281. As indicated, a peptide or peptides can be selected and used which includes one or more of these glycation sites and/or others. Other glycation sites include, for example, accessible arginine residues and other accessible lysine residues. It is useful to determine the fraction of the albumin glycated at one or more residues instead of determining an absolute level of glycation. Using fraction glycated helps eliminate some sources of variability, including much of the patient-to-patient and sample treatment variabilities.

The various glycation sites can be glycated at different rates and therefore can be glycated to differing extents which depend on the average blood glucose concentrations. As a result, multiple glycation sites may be used in combination to determine glycation patterns and/or extent of glycation. Similar to single glycation site analysis, it is useful to determine the glycation ratio for each site. That is, the ratio of glycated residue to un-glycated residue at each site is determined. At low blood glucose levels, only the more susceptible residue or residues will be glycated, e.g., the 5-terminal residue. At higher blood glucose levels, a progressively greater proportion of the more susceptible residues will be glycated, and the moderately susceptible residues will begin to be glycated. At still higher blood glucose levels, the most susceptible residues will be glycated to an even greater degree, a progressively greater fraction of the moderately susceptible residues will be glycated, and the weakly susceptible residues will begin to be glycated. As a result, the glycation pattern and/or the extent of each of a set of residues subject to glycation can be used to provide confirmatory and/or additional information on average blood glucose levels. This can be useful, for example, for monitoring the efficacy of different medical or lifestyle intervention strategies and/or risks to the patient.

C. Assay Precision Control

Sample treatment can include dilution of the sample to provide appropriate reduced concentrations of analyte for detection. In some embodiments, the dilution is selected to be compatible with the sensitivity and dynamic range of the assay to be used. It is helpful to utilize an assay which provides at least 4, 4.5, or 5 orders of magnitude dynamic range of signal, or even greater range.

More generally, by using appropriate sample dilution, label loading, and detection zone construction with an appropriate label in a broad dynamic range detection system, the relevant (e.g., clinically relevant) analyte concentration range can be expanded over the detectable signal dynamic range, resulting in enhanced clinical precision. This advantage can be obtained because over a large range the imprecision due to the assay and detection system is relatively constant. Thus, in doing this, it is desirable to avoid zones on the signal-concentration curve where system noise becomes significantly higher. This approach can be used in many assay applications, e.g., where the relevant magnitude of the concentration range is substantially smaller than the dynamic range of the detection system. Thus, for example, if the relevant concentration range extends over 1 or 2 orders of magnitude, while the signal dynamic range of the system is 5 orders of magnitude, the signal corresponding to the 1 or 2 orders of magnitude can be expanded over the 5 orders of the signal range.

The signal-concentration curve slope can be adjusted by adjusting any of several different parameters. In many cases, the slope and the positioning of the signal-concentration are adjusted such that the signal corresponding to the highest concentration of interest will be at or near the top of the dynamic range of the detection system (this would normally be reversed for a competitive-type assay). In this way the full dynamic range of the system can be utilized or at least moves the signal range corresponding to the analyte concentration range of interest away from the low signal regime. A result of this is to reduce the relative effect of intrinsic system noise.

The high signal point can be adjusted in various ways. These include, for example, sample dilution and/or sample size, which adjusts the amount of analyte in the sample and therefore the amount of sample which will be labeled for detection (assuming the assay system is not overloaded with analyte).

Alternatively or in addition, the signal per analyte can be adjusted, e.g., by selection of detectable label (i.e., differing signal intensities per label moiety), signal amplification, adjustment of the number of capture sites, and/or adjustment of the number of signal generating moieties per analyte.

DEFINITIONS

"Total protein" refers to the total amount of a particular (e.g., hemoglobin) protein in a sample regardless of whether the protein is glycated or not. A "peptide corresponding to total protein" refers to a peptide portion of the protein of interest (e.g., hemoglobin) that when detected is representative of the amount of the protein in the sample. Such a peptide will generally be a portion of the protein not comprising a potential site for glycation of the protein.

As used herein, the term "assay device" (also referred to as an "assay cartridge" or simply "cartridge") refers to a device used in performance of an assay which includes locations on and/or in the device for application of sample, reaction, and signal reading. In many but not all assay devices, there will be a location zone where analyte is immobilized, e.g, in most lateral flow assay devices.

The term "label" is used in a manner common for biological or biochemical assays, and refers to a moiety of a molecule or complex that is directly or indirectly detectable in a manner providing detection of the presence or amount of the label present. Examples include fluorophores, chemiluminescent moieties, light absorbing moieties, resonance light scattering particles, enzymes, and the like, as well as specific binding moieties such as biotin which can be used to link another moiety for detection. As used herein, the term "detectable label" is equivalent to the term "label". Indication that a label is "directly detectable" means that the the label is directly involved in signal generation (e.g., a fluorophone or a moiety having characteristic light absorbing, reflecting, or scattering properties, or a radioactive moiety). In contrast, an "indirectly detectable" label requires the presence of at least one additional substance for a detectable signal to be generated. Examples of indirectly detectable labels include an enzyme which reacts with a substrate to produce a colored, fluorescent, or chemiluminescent species, and a specific binding moiety which specifically binds with the other of a specific binding pair thereby associating a signal generating substance or moiety with the indirect label.

The term "full-coated label" refers to a construct, often a particle, which bears or includes detectable moieties and which is either a layered label as defined below or has at least one protein coating which is substantially fully linked to the surface below (i.e., a "fully linked coating label"), e.g., to the particle surface. In most cases, the protein will be fully linked through amines, e.g., such that accessible amines are substantially depleted. In most cases, such a full-coated label has one or more coatings which essentially fully cover the coated particle or interior portions of a layered construct which does not have a solid phase particle core.

The term "layered label" refers to a construct, usually a particle, which bears or includes detectable moieties and which has at least two layers of a polymer material or materials. In many cases, there are covalent links between the layers. In most cases, the layers will be hydrophilic. The layered label may have a core particle, e.g., a polystyrene particle, or may be formed without a core. The detectable moieties may, for example, be covered by the layers, and/or may be distributed in or between layers. For layered labels having a core particle and detectable moieties covered by the layers, detectable moieties may be embedded in the core particles and/or on the surface of the core particles.

The term "staged label" refers to a construct, often a particle, which is protein coated with covalently linked protein. The protein is attached in a manner which essentially depletes functional groups of at least one type in the protein.

Additional functional groups are then created in the protein, e.g., by reduction of disulfide bonds. Such constructs, e.g., particles, bear or include detectable moieties. The protein coating has one or more additional moieties linked through —SH groups resulting from reduction of the disulfide bonds or through functional groups derived from such reduced disulfide bonds. Such additional moieties may be of various types, for example, members of specific binding pairs (e.g., antigen for an antigen-antibody pair, or biotin for a streptavidin pair), detectable moieties, or additional coating species, which may be of the same or different protein or of a different type, e.g., a polysaccharide or synthetic polymer.

The terms "lateral flow assay" and "strip assay" are used herein equivalently to refer to assay formats, usually immunoassays, in which the test sample flows along a solid phase substrate (usually a membrane such as nitrocellulose, which may be adhered to a backing material impervious to the liquid used in the assay) via capillary action from a sample application zone into a fluid sink. The sample commonly encounters a detection reagent (commonly dried in a reagent pad downstream of the sample application zone; commonly a coloured reagent) which mixes with the sample and transits the solid phase substrate encountering one or more lines or zones which have been pretreated with an appropriate specific binding moiety (typically an antibody or antigen).

Depending upon the analytes present in the sample, the detection reagent can become bound at the test line or zone. After passing over the detection lines or zones, the fluid goes into a fluid sink (commonly an absorbent material).

The term "analyte" is used herein in the usual manner for in vitro biological assays, referring to a substance, e.g., an ion, molecule, or complex, which is detected and/or quantitated or at least intended to be detected and/or quantitated in an assay.

As used herein, the term "analyte-specific binding reagent" and "analyte-binding agent" refer to a molecule or complex that specifically binds to desired analyte, and may also include moieties having other functions, such as labeling the molecule or complex. In some, but not all embodiments, the analyte-binding agent undergoes a detectable structural change upon binding analyte (e.g., an allosteric structural change).

The term "antibody" is used herein in the broadest sense and is intended to include intact monoclonal antibodies and polyclonal antibodies, as well as derivatives, variants, fragments and/or any other modification thereof so long as they exhibit the desired binding activity. Antibodies encompass immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and Fab2 fragments, and a Fab expression library. Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types.

Antibodies may be derived from a variety of sources, e.g., human, goat, mouse, rabbit, rat, sheep, camellid, and shark among others. Also included are chimeric antibodies, for example, monoclonal antibodies or modifications thereof that are specific to more than one source, e.g., a mouse or human sequence. Further included are camelid antibodies or nanobodies. Antibodies also include multi-specific, e.g., bispecific (e.g., multivalent, or multimeric) antibodies and functional fragments thereof. It will be understood that each reference to "antibodies" or any like term, herein includes intact antibodies, as well as any modifications thereof.

As used in connection with the present invention, the terms "glycation" and "glycated" and the like refer to non-enzymatic glycolsylation.

Reference to a "fraction of glycated protein in a sample" and like terms means, for a particular identified protein, the ratio of the level of glycated protein to the level of total protein, or alternatively ratio of glycated protein to un-glycated protein. The ratio may be expressed in various ways, e.g., as conventional fraction, decimal fraction, or as percentage. In many cases, the determinations of the levels of glycated protein, un-glycated protein, and/or total protein are carried out using peptide fragments of the protein.

In connection with the present assays, the term "total protein" refers to the level of a particular protein whether the protein is glycated or not glycated, and does not refer to the combined level of all proteins in a sample or in an organism(s) from which a sample is taken.

Indication that a protein or peptide is "susceptible to glycation" means that the protein or peptide contains at least one site or residue which can be glycated in vivo under conditions of high blood glucose, preferably blood glucose in a clinically significant range. Non-limiting examples of such glycation sites are the N-terminal amino acids of hemoglobin beta-chains. In many cases, the amine side changes of exposed lysine residues can be glycated in vivo.

In the context of this invention, reference is made to peptides cleaved from sample protein (which can be referred to as "sample peptides") and to peptides used to compete for binding with the sample peptides (which can be referred to as "competitive peptides"). For a particular sample peptide, the competitive peptide need not be identical (e.g., it may be a different length), but instead it behaves substantially the same with respect to the assay-critical characteristics, e.g., antibody binding. For example, an N-terminal peptide cleaved from sample protein may be longer or shorter than the corresponding competitive peptide and/or the competitive peptide may be biotinylated and the sample peptide not biotinylated, but both bind substantially equivalently to the corresponding antibody.

For proteins or polypeptides which have different isoforms, a "characteristic isoform peptide" is a peptide which includes a sequence corresponding to a sequence of the polypeptide with a mutated residue characteristic of the particular isoform together with additional amino acid residues corresponding to the polypeptide on one or both sides of the mutated residue. For example, for HbS, a characteristic HbS isoform peptide will include the E6V residue together with adjacent Hb aa sequence on one or both sides of the valine residue. The term applies to both peptides digested from fully length polypeptide and synthetic peptides.

Reference is made herein to an "unglycated version" of a protein or peptide and to a "glycated version" of the protein or peptide. A "glycated version" means a particular protein or peptide which is glycated, while "un-glycated version" refers to the same protein or peptide which is not glycated, or at least is not glycated at a site to be detected in the relevant assay.

In the context of this invention, the term "competitive binding conditions" refers to assay conditions in which members of specific binding pairs are brought into contact in solution or suspension, and in which two distinguishable members of specific binding pairs are present such that they effectively compete with each other for binding to the cognate member of the specific binding pair. For example, in the Hb A1c peptide competitive assay, the conditions are such that N-terminal peptide from the sample effectively competes with immobilized or immobilizable N-terminal peptide for binding to the corresponding labeled antibody.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to the particular labels used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values or value range endpoints are provided for embodiments, additional embodiments are described by taking any 2 different values as the endpoints of a range or by taking two different range endpoints from specified ranges as the endpoints of an additional range. Such ranges are also within the scope of the described invention. Further, specification of a numerical range including values greater than one includes specific description of each integer value within that range.

Thus, additional embodiments are within the scope of the invention and within the following claims.

What is claimed is:

1. A method for determining the fraction of a glycated protein in a sample, comprising
    contacting (i) a labeled, specific binding member specific for total protein or a peptide corresponding to total protein or un-glycated protein or peptide, and (ii) a labeled, specific binding member specific for glycated protein or peptide with
    a) a sample containing said protein or a peptide of said protein susceptible to glycation; and
    b) a non-sample-derived glycated version of said protein or peptide; or
    c) a non-sample-derived unglycated version of said protein or peptide;
    detecting a plurality of signals, with at least a first signal indicative of the level of glycated protein, and at least a second signal indicative of the level of total protein or unglycated protein; and
    determining a ratio between glycated protein and un-glycated protein, or between glycated protein and total protein, as an indication of the fraction of said protein which is glycated in said sample,
    wherein said contacting is performed under competitive binding conditions, and wherein said first signal and said second signal are distinguishable; and
    wherein the sample is contacted with a control labeled binding member that specifically binds a target not in the sample and said control labeled binding member is later detected, wherein the detected amount of control labeled binding member is used to normalize signals for the level of glycated protein or total protein or both.

2. The method of claim 1, wherein said peptide is cleaved by trypsin, endopeptidase GluC, pepsin, or a prolyl endopeptidase.

3. The method of claim 1, wherein said first and second signals are fluorescent signals or TRF signals.

4. The method of claim 1, wherein said detecting is performed on a lateral flow assay device, wherein said device comprises a detection zone comprising an immobilization site for glycated protein or peptide and an immobilization site for said total protein or peptide corresponding to total protein, wherein signal corresponding to glycated protein or peptide and signal corresponding to the total protein or the peptide corresponding to total protein, are detected separately.

5. The method of claim 4, wherein said control labeled binding member is immobilized in an immobilization site comprising immobilized versions of the target not in the sample.

6. The method of claim 5, wherein said target not in the sample is a protein from a non-human species.

7. The method of claim 1, wherein said detecting is performed on a lateral flow assay device, wherein said device comprises a detection zone comprising an immobilization site for glycated protein or peptide and an immobilization site for un-glycated protein or peptide, wherein signal corresponding to glycated protein or peptide and signal corresponding to un-glycated protein or peptide are detected separately.

8. The method of claim 1, wherein a plurality of isoforms of said protein or a peptide thereof are distinguishably detected.

9. The method of claim 8, wherein said plurality of isoforms are detected in a single zone.

10. The method of claim 8, wherein said isoforms are detected in separate zones.

11. The method of claim 8, wherein said protein is hemoglobin beta-chain and said isoforms include at least two of HbA, HbC, HbD Punjab, HbE, and HbS.

12. The method of claim 1, wherein said protein is human hemoglobin.

13. The method of claim 12, wherein said glycated peptide is HbA1C N-terminal peptide.

14. The method of claim 1, wherein a plurality of isoforms of said protein or a peptide thereof are distinguishably detected.

15. The method of claim 14, wherein said protein is hemoglobin beta-chain and said isoforms include at least two of HbA, HbC, HbD Punjab, HbE, and HbS.

16. The method of claim 14, wherein said protein is hemoglobin beta-chain and said isoforms include HbC, HbD Punjab, HbE, and HbS.

17. The method of claim 8, wherein said protein is hemoglobin beta-chain and said isoforms include HbE and HbS.

18. The method of claim 1, wherein the sample is from a human and the target not in the sample is a protein from a non-human species.

* * * * *